United States Patent [19]

Roseman et al.

[11] 4,237,888

[45] Dec. 9, 1980

[54] TWO-MEMBRANE MEDICATED DEVICE FOR RATE-CONTROLLED ADMINISTRATION OF PROSTAGLANDINS

[75] Inventors: Theodore J. Roseman, Portage; Osmer C. Carpenter, Schoolcraft Township, Kalamazoo County, both of Mich.; Richard W. Baker, Bend; James W. Ayres, Corvalis, both of Oreg.

[73] Assignee: The Upjohn Company, Kalamazoo, Mich.

[21] Appl. No.: 23,126

[22] Filed: Mar. 23, 1979

[51] Int. Cl.$^3$ .............................................. A61F 13/20
[52] U.S. Cl. .................................................. 128/270
[58] Field of Search .............................. 128/260–270, 128/285; 424/16, 19–28, 32

[56] References Cited

U.S. PATENT DOCUMENTS

| | | | |
|---|---|---|---|
| 3,490,454 | 1/1970 | Goldfarb et al. | 128/260 |
| 3,854,480 | 12/1974 | Zaffaroni | 128/260 |
| 3,948,254 | 4/1976 | Zaffaroni | 128/271 |
| 3,993,073 | 11/1976 | Zaffaroni | 128/270 |

Primary Examiner—C. Fred Rosenbaum
Attorney, Agent, or Firm—Robert A. Armitage

[57] ABSTRACT

The present specification describes a medicated device adapted for a single, acute, and rate-controlled rectal or vaginal administration to a mammal of a lipophilic prostaglandin. The device accomplishes drug administration at an essentially time-independent rate of dosage. Further, the device advantageously results in the substantial exhaustion of the prostaglandin from the device at the conclusion of the single, acute use. The device comprises three elements:

(A) an inert resilient support means contoured for easy vaginal or rectal insertion;
(B) a first flexible polymer film layer affixed to the support means and containing the prostaglandin dispersed therethrough, this first polymer film not being rate limiting as to the release of drug from the device; and
(C) a second polymer film, laminated onto the first polymer film and providing a release rate therefrom of prostaglandin, which is rate limiting both as to the release of prostaglandin from the device and absorption rate by the rectal or vaginal tissues.

2 Claims, 3 Drawing Figures

TWO-MEMBRANE MEDICATED DEVICE FOR RATE-CONTROLLED ADMINISTRATION OF PROSTAGLANDINS

DESCRIPTION

BACKGROUND OF THE INVENTION

The present invention relates to a device for a single, acute delivery of a LAP (lipophilic anti-luteal/oxytocic prostaglandin) for the induction of a discrete physiological event in a mammal. The invention further relates to a controlled drug-delivery device, whereby the rate of dosage delivered is essentially time-independent.

The invention further relates to the method of use of the aforementioned device for uses in the reproductive cycle, e.g., obstetrical and gynecologic purposes. In particular, the invention relates to the use of the present device and the regulation of the mammalian estrous or menstrual cycle, pregnancy interruption during the first or second trimester, the induction of labor at term, cervical dilatation, and evacuation of the uterine contents necessitated by fetal death in utero or hydatidiform mole. Hence the invention relates to the acute use of antifertility prostaglandins for the induction of discrete obstetric or gynecologic events. The present invention is therefore contrasted to chronic uses of pharmacologic agents for such purposes as suppressing ovulation in otherwise menstruating females and the like.

PRIOR ART

Rectal or vaginal administration of therapeutic doses of numerous pharmacological agents is accomplished in a rate-controlled, time-independent manner employing numerous medicated devices. As will become apparent, however, none of these prior art devices will exhibit all of the various advantages and adaptations for use present in devices in accordance with the present invention.

Such rate-controlled release devices are in contrast to other drug delivery means such as suppositories formulated for either rectal or vaginal use. Suppositories release a therapeutic agent contained therein as they melt down in the cavity into which they are placed. Hence the release rate from suppositories is not rate-controlled, being subject to the vagaries of the cavity into which they are inserted, much less time-independent. In this respect, suppositories are clearly distinguished from the novel devices herein.

The prior art devices exhibiting rate-controlled release of a therapeutically active agent typically operate by encasing a drug reservoir with a drug-permeable, or otherwise drug-porous barrier. See for example U.S. Pat. No. 3,279,996, describing a drug encapsulated in polymeric walls through which diffusion therethrough results in a rate-controlled release. Other such rate-controlled membrane devices include those specifically adapted for the prolonged release of drug from a drug-bearing reservoir, and include those of U.S. Pat. No. 3,948,254, describing a reservoir of a solid drug carrier; U.S. Pat. No. 3,926,188, describing a low water-soluble crystalline drug in a polymeric core lamina and interposed between release rate-controlling laminae; U.S. Pat. No. 3,710,795, describing a polymeric matrix with drug dispersed therethrough and being stressed by an elastic, rate-controlling membrane; U.S. Pat. No. 3,903,880, describing a drug matrix reservoir enclosed in a vinylene-ethyl acetate copolymer barrier; U.S. Pat. No. 3,938,515, describing a drug with carrier enclosed with a polymeric membrane containing a permeability-modifying polymeric additive (e.g., a polyester); U.S. Pat. No. 3,911,911, describing capsules with permeable walls of a silicone elastomer containing therewithin progestational agents; and U.S. Pat. No. 3,854,480, describing a polymeric matrix containing drug particles dispersed therethrough and surrounded by a drug-permeable membrane.

Numerous vaginal devices are known in the art, particularly for the supply of either prostaglandins or progestational agents. These devices include those described in U.S. Pat. No. 3,915,898, wherein a sponge impregnated with a progestational compound is disclosed. In contrast to the device of the present invention, the drug-bearing sponge does not provide a controlled release therefrom.

Other examples of vaginal devices known in the art for the delivery of drug therefrom include medicated vaginal tampons, for example those of U.S. Pat. No. 3,902,493 and British Pat. No. 1,480,615 (Derwent Farmdoc CPI No. 79338V), where drug-bearing film coating of an ordinary catamenial tampon is disclosed. Controlled release devices do, however, include those of U.S. Pat. No. 3,920,805, disclosing prostaglandin-containing silastic rings wherein the outer surface of said ring has a prostaglandin dispersed therethrough, and U.S. Pat. No. 4,043,339, describing disc-like silastic elastomers containing prostaglandins imbedded therewithin.

Other devices, specifically adapted for the prolonged release of drug, but not exhibiting a rate-controlled membrane, include devices described in U.S. Pat. No. 3,921,636, describing a polymeric matrix through which drug is released from drug reservoirs contained therewithin, and U.S. Pat. No. 3,978,203, describing drug-containing biodegradable and metabolizable polymeric matrices. Other devices containing polymeric and drug matrices include those described in U.S. Pat. No. 3,975,350, wherein hydrophilic polyurethane systems are disclosed.

There are further known in the art ophthalmic devices providing a time-independent controlled rate of release of drug from such devices such as are described in U.S. Pat. No. 3,641,237. In particular, these ophthalmic devices comprise an inner drug-bearing film layer encapsulated by a water-swellable polymeric matrix in film form and laminated to the drug bearing film for the delivery of water-soluble ophthalmic drugs. Likewise there is described in U.S. Pat. No. 3,630,220 ophthalmic devices comprising an inner drug reservoir, which is rate-controlling as to the release of drug from the device, and an outer hydrophilic polymeric membrane, which provides compatability of the device with the ocular tissues.

SUMMARY OF THE INVENTION

The present invention provides a novel device for the delivery of pharmacological agents. Particularly, the present invention provides devices adapted for rectal or vaginal use. Further, the present invention specifically provides for medicated devices whereby lipophilic therapeutic agents are administered vaginally or rectally. Most particularly, the present invention relates to medicated devices for the vaginal or rectal administration of lipophilic anti-luteal/oxytocic prostaglandins.

The present invention further relates to medicated devices adapted for a single and acute administration. Moreover, the invention particularly provides medicated devices wherein the release rate therefrom is rate-controlled and essentially time-independent during the course of therapeutic use therefrom.

The present invention most particularly relates to medicated devices comprising three components: two membranes and a support means. Particularly, the present invention relates to medicated devices exhibiting two flexible polymeric membranes, one serving as a drug-bearing membrane, the other a rate-controlling membrane.

Most particularly, the present invention provides:

a medicated device adapted for a single, acute, and rate-controlled vaginal or rectal administration to a female mammal of a therapeutic amount of a LAP (lipophilic anti-luteal/oxytocic prostaglandin) effective to accomplish a discrete event in the mammalian reproductive cycle;

said administration being of a predetermined TD (therapeutic duration);

said administration resulting in the release of LAP from said device during the course of said administration at a predetermined, essentially time-independent RR (release rate); and said administration resulting in the exhaustion of said LAP from said device during the course of said treatment to the extent that the medicinal reuse of said device is essentially impossible; which comprises:

(1) a flexible polymeric DBM (drug-bearing membrane), containing dissolved and suspended therethrough said LAP and being further characterized by:
 (a) a $D_{DBM}$ (diffusion coefficient of said DBM with respect to said LAP) and an $S_{DBM}$ (solubility in said DBM of said LAP);
 (b) an SA (surface area) of said DBM sufficiently great such that the RF (release flux of said LAP released from said device), which RF is the quotient which is said RR divided by said SA, is substantially less than the absorption rate per unit area of said LAP by the rectal or vaginal epithelial tissues of said mammal in contact with said device during said administration; and
 (c) an essentially uniform $T_{DBM}$ (thickness of said DBM) and a $D_{DBM}$, (initial concentration of said LAP in said device), which $C_{DBM}$ is the quotient which is the amount of said LAP divided by the volume of said DBM;

(2) a flexible, polymeric RCM (rate controlling membrane), being laminated onto a first surface of said DBM and being substantially coextensive therewith, being further characterized by:
 (a) an $S_{RCM}$ (solubility in said RCM of said LAP) and an essentially uniform $T_{RCM}$ (thickness of said RCM); and
 (b) $D_{RCM}$ (diffusion coefficient of said RCM with respect to said LAP), such that the $R_{RCM}$ (resistance of said RCM), which $R_{RCM}$ is the quotient which is said $T_{RCM}$ divided by the products of (i) K (partition coefficient between said DBM and RCM), which is the quotient which is said $S_{DBM}$ divided by said $S_{RCM}$, and (ii) said $D_{RCM}$ is at least very much greater than the $R_{DBM}$ (resistance of said DBM), which $R_{DBM}$ is the quotient which is said $T_{DBM}$ divided by said $D_{DBM}$; and (3) a physiologically inert, resilient, and water-insoluble support means, having the second surface of said DBM laminally affixed to at least a portion of the surface thereof; being adapted, contoured, and dimensioned for accomodation of the entirety of said DBM on the surface thereof and for easy and comfortable rectal or vaginal insertion and withdrawal of said device; being essentially non-absorptive of said LAP; and being of substantially non-concave construction, whereby the surface of said device upon insertion is in essentially complete and intimate contact with rectal or vaginal epithelial tissues and associated secretions;

said device being further characterized by
 (a) said $T_{RCM}$ being approximately $$(D_{RCM} S_{RCM}/RF) \qquad \text{Eq. 1}$$

wherein RF, $D_{RCM}$ and $S_{RCM}$ are as defined above;

(b) a $T_{50}$, which is the time after TD for the RF to be reduced by 50 percent, being approximately $$(\ln 2)\,[P/(1-P)](TD) \qquad \text{Eq. 2}$$

wherein P is the ratio of the amount of LAP remaining in said device at TD to the initial amount of LAP in said device, said P being characterized by a preselected value less than about 0.42; and wherein TD is as defined above;
 (c) said $T_{DBM}$ being approximately $$[P/(1-P)][(RF)(TD)/S_{DBM}] - T_{RCM}/2K \qquad \text{Eq. 3}$$

wherein K, TD, $T_{RCM}$, RF, and P are as defined above; and (d) said $C_{DBM}$ being approximately $$((RF)(TD)/(1-P)T_{DBM}) \qquad \text{Eq. 4}$$

wherein P, RF, TD, and $T_{DBM}$ are as defined above.

As indicated above, devices in accordance with the present invention are specifically adapted for the rectal or vaginal administration of lipophilic pharmacological agents, particularly lipophilic anti-luteal/oxytocic prostaglandins. For the purposes of the present invention, pharmacological agents are considered prostaglandins provided they represent either a naturally-occurring prostaglandin or a chemical and pharmacological analog thereof. For the purposes of the present invention, natural prostaglandins are those biosynthetic derivatives of unsaturated fatty acids exhibiting anti-luteal or oxytocic properties. Thus the naturally-occurring prostaglandins include prostaglandin A compounds, prostaglandin R compounds, prostaglandin C compounds, prostaglandin D compounds, prostaglandin F compounds, prostaglandin F compounds, thromboxanes, and prostacyclins. Prostaglandin analogs therefore include chemically modified substances which retain the characteristic antiluteal or oxytocic properties of the natural prostaglandins. For the purposes of the present invention, prostaglandin analogs are considered to retain the anti-luteal or oxytocic property of the corresponding natural prostaglandin provided that the potency of these analogs in the standard laboratory animal tests, hereinafter described, is at least 0.1 times the potency of prostaglandin $E_2$ or prostaglandin $F_2$.

The therapeutic agent in accordance with the present invention is considered an anti-luteal/oxytocic prostaglandin provided that it is either a natural prostaglandin or an analog thereof retaining at least one-tenth the anti-luteal or oxytocic potency of either prostaglandin F₂ or prostaglandin E₂. The anti-luteal potency of a natural prostaglandin or an analog thereof is assessed by its potency in standard laboratory tests designed to meausre luteolytic activity or the ability to cause regression of the corpus luteum. The standard experimental animal of convenience for assessing anti-luteal effects is the Golden hamster, an animal in which prostaglandins, such as PGF₂, are known to terminate early pregnancy by a direct lytic effect on the corpus luteum. While the use of the Golden hamster as an experimental animal for assessing the anti-luteal effects of prostaglandins is widely known, see U.S. Pat. No. 3,852,465 for a description of one such procedure.

The oxytocic potency of natural prostaglandins or analogs thereof is assessed in accordance with the present invention by the effect of these agents on the pregnant mammalian myometrium. The standard laboratory animal of choice for assessing oxytocic potency is the Rhesus monkey (Macaca mulatta). Tests on the pregnant female Rhesus monkey designed to measure the amplitude and frequency of uterine contractions upon administration of a naturally-occurring prostaglandin or analog thereof are widely known, e.g., Kirton, et al., New York Academy of Science 180:455 (1971), Fuchs, et al., New York Academy of Science 180:531 (1971), and Kirton, et al., Prostaglandins 1:319 (1972).

The lipophilicity of the anti-luteal/oxytocic prostaglandins in accordance with the present invention is determined by standard techniques. One especially simple and convenient technique in accordance with the present invention for assessing lipophilicity is the determination of the n-octanol water partition coefficient. This partition coefficient is determined by placing the anti-luteal/oxytocic prostaglandin in an equilibrated mixture of n-octanol and water, shaking the mixture until equilibrium and thereafter measuring the concentration ratio as between the n-octanol and water layers. The procedure is advantageously carried out at ambient temperature (preferably about 25° C.) and the quantity of prostaglandins selected is less than the quantity soluble in the aqueous layer. The larger the ratio (concentration in n-octanol:concentration in water), the greater the lipophilicity. A natural prostaglandin or an analog thereof is deemed lipophilic provided its partition coefficient, i.e., ratio of the concentration in n-octanol to the concentration in water, is about equal to or greater than that of prostaglandin F₂ in free acid form. For natural prostaglandins or analogs thereof which are carboxylic acids, lipophilicity may bne modified by derivitization of the carboxylic acid to its ester form. For example, prostaglandin F₂, methyl ester, is significantly more lipophilic than prostaglandin F₂ in its free acid form. Thus for those anti-luteal/oxytocic prostaglandins which are less lipophilic than PGF₂, esters thereof which are about equally lipophilic or more lipophilic than PGF₂ are contemplated for use in accordance with the present invention.

In accordance, therefore, with the aforementioned criteria, natural prostaglandins or analogs thereof which are both lipophilic and anti-luteal/oxytocic are considered to be LAP's or lipophilic anti-luteral/oxytocic prostaglandins in accordance with the present invention.

A LAP of the present invention is employed to accomplish a discrete event in the mammalian reproductive cycle. While the treatment of humans is especially contemplated by medicated devices in accordance with the present invention, domestic animals and other mammalian species are also contemplated as subjects for use of devices of the present invention. The discrete events in the mammalian reproductive cycle induced by the employment of devices of the present invention are those physiological events which can be induced by LAP administration of about 72 hr. or less. Particularly, such discrete events are those which can be induced by LAP administration with devices of the present invention in 24 hr. or less. Such discrete events in the mammalian reproductive cycle include regression of a corpus luteum in estrous-cycling animals, abortion, labor induction, hydatidiform mole removal, uterine evacuation following fetal death in utero, cervical dilatation (e.g., preliminary to a dilatation and curretage), and treatment of purulent genital tract diseases of domestic animals (e.g., pyometra). For each of these various indications, the necessary dosage of a LAP and its required duration of administration upon vaginal or rectal administration can be readily assessed. One particularly convenient means for assessing the necessary dosage and duration of treatment is by determination of the relative amount of LAP required to stimulate the uterus of the pregnant Rhesus monkey upon to stimulate the uterus of the pregnant Rhesus monkey upon vaginal administration.

Once a particular LAP has been selected and the discrete event in the mammalian reproductive cycle for treatment is confronted, the desired release rate (RR) from the device in accordance with the present invention and therapeutic duration of treatment (TD) are selected. While the precise and optimal (i.e., acceptable therapeutic effect with minimization of side effects) release rate will vary depending upon the particular mammal and the precise therapeutic duration of treatment and may vary by up to about 50 percent from mammal to mammal, these values are nonetheless predetermined based upon experience and the known pharmacological actions of the particular LAP. Especially important is the known potency of the particular LAP on vaginal administration to the Rhesus monkey, as indicated previously. Accordingly, the ordinarily skilled physician or veterinarian will readily appreciate the factors relevant to determining both the release rate and therapeutic duration of treatment and select appropriate values for each employing ordinary skill of those from this profession. For example, where relatively shorter therapeutic durations of treatment are indicated (e.g., indicated induction of labor for patients presenting toxemia of pregnancy), somewhat higher release rates of a particular LAP (especially a LAP, such as prostaglandin E₂, which is hypotensive) will be readily appreciated and selected.

As indicated previously, a medicated device in accordance with the present invention provides for a rate-controlled, essentially time-independent release rate during the therapeutic duration of treatment. While a rate-controlled release makes reference to the absence of an effect on release rate from the vagaries of the cavity into which the medicated device is placed during its therapeutic use, the essentially time-independent release makes reference to the constancy of the release rate from the initiation of treatment until the end of therapeutic duration of treatment. Accordingly, the release rate from the device, essentially a preset constant value, is hereinafter designated as "RR". Likewise, the predetermined therapeutic duration of treatment is designated hereinafter as "TD". The product of these two predetermined values (RR×TD) is the therapeutic amount of the LAP delivered by the device for accomplishing the discrete event in the mammalian reproductive cycle.

Devices constructed in accordance with the present invention contain two flexible polymeric membranes; a drug-bearing membrane (DBM) and a rate-controlling membrane (RCM). Such flexible polymeric membranes are characterized by certain readily ascertained physical properties with respect to a LAP. In particular, the polymers are characterized by a diffusion coefficient with respect to a particular LAP and a solubility for a particular LAP in the polymer. Also in the construction of devices in accordance with the present invention these flexible polymeric membranes will exhibit an essentially uniform thickness. Hence the polymeric membranes will further exhibit resistances to the diffusion of a particular LAP therethrough, which respective resistances are defined as the quotient obtained by dividing the thickness of the particular LAP by its diffusion coefficient.

Polymers are selected for use in devices of the present invention based firstly on their ability to solubilize the desired LAP and to permit the diffusion of the LAP therethrough. Accordingly, any of the polymeric substances known in the art to be used in delivery devices for lipophilic drugs are readily employed by the present invention. Polymers are therefore broadly selected from numerous classes of compounds, including the polyurethanes, styrene-butadiene block copolymers, polyesters, polysiloxanes, polyvinyl chlorides, ethylene vinyl acetates, and polyalkylenes. As is apparent by reference to the above list of suitable polymers, the range of substances is limited only by the ability of a particular polymer to solubilize and diffuse the LAP.

Secondly, the two polymers selected must preferably exhibit substantially different diffusion coefficients so that the relative resistance in the DBM ($R_{DBM}$) is at least very much less than the resistance in the RCM ($R_{RCM}$). For this purpose a membrane resistance is defined as the quotient of the thickness divided by the diffusion coefficient for DBM and thickness divided by the product of the diffusion coefficient and the partition coefficient for $R_{RCM}$. Therefore, for two polymers of significantly different resistances, the polymer which will serve as the DBM is selected as the polymer exhibiting the lower diffusion coefficient, reserving the polymer with the highest diffusion coefficient for the RCM. Diffusion coefficients are preferred where $R_{RCM}$ is at least 10 and more preferably at least 100 times the $R_{DBM}$.

As is apparent from the foregoing discussion regarding the relative resistances of the DBM and RCM, the necessary constraints on resistances are rigorously satisfied not only by reference to the relative diffusion coefficients, but is further established by consideration of the relative membrane thickness. These relative membrane thicknesses are determined by certain mathematical expressions which provide approximate values therefor. With respect to the thickness of the rate-controlling membrane, $T_{RCM}$, its value is given approximately by Eq. 1, while the thickness of the drug-bearing membrane, $T_{DBM}$, is given approximately by Eq. 3. With regard to Eq. 1 and 3 above, $D_{RCM}$ is the diffusion coefficient for the RCM while TD and RF are as defined above. Finally, K, the partition coefficient, represents the ratio which is the quotient of the solubility of LAP in the drug-bearing membrane ($S_{DBM}$) divided by its solubility in the rate-controlling membrane ($S_{RCM}$). P is a fraction determined by methods discussed below.

The solubilities and diffusion coefficients for polymers employed in the construction of devices in accordance with the present invention are determined by standard experimental means. For example, a two-cell diffusion chamber is readily employed in the determination of the diffusion coefficient and solubility of any polymer with respect to a particular LAP. Briefly, the two-cell diffusion chamber consists of a polymeric membrane which separates the chamber's two cells. One cell contains an inert medium with the LAP dissolved therethrough and maintained at a constant concentration and the other cell contains only the inert medium itself. The concentration of drug in the second cell is then plotted as a function of time, from the time at which the chamber is assembled. After an initial non-linear phase, the concentration of LAP in the second cell is a linear function of time. For this linear function, the slope and abscissa (time-axis) intercept or time lag (TL) can be determined graphically, and represent respectively:

$$\text{slope} = D_{RCM} S_{RCM}/T; \quad TL = T^2/6D_{RCM},$$

wherein T represents the thickness of the RCM in the chamber. The corresponding DBM characteristics are determined identically.

Having thusly determined the diffusion coefficients and solubilities of the polymeric membranes, the predetermined, time-independent release flux of drug from the device during administration is thereafter determined. The release flux hereinafter "RF", is defined as the release rate of drug from the device per unit area of the DBM. As indicated above, release rates for devices in accordance with the present invention are determined for each of the LAP's, based primarily on the potency of the LAP and the desired therapeutic duration of treatment and are ordinarily between 1 μg/hr and 1 mg/hr.

One constraint in designing devices in accordance with the present invention is the provision of a surface area for the device, particularly the drug-bearing membrane thereof, which is sufficiently large as to permit a relatively small release flux from the device. The release flux from the device is the release rate of LAP from the device per unit surface area of the drug-bearing membrane of the device. The release flux from the device is the release rate of LAP from the device per unit surface area of the drug-bearing membrane of the device. Such relatively small release rates from the device assure that the animal or patient in whom the device is placed will achieve a substantially uniform, time-independent absorption of the LAP. Accordingly, release fluxes from the device are selected such that the release flux or RF is substantially less than the absorption rate per unit area of the rectal or vaginal epithelial tissues of the mammal in whom the device is being administered. Within the range of release rates ordinarily employed with devices in accordance with the present invention, devices exhibiting a surface area (SA) of the drug-bearing membrane thereof on the order of 10–50 cm$^2$ are ordinarily sufficient.

A further characteristic of a device in accordance with the present invention is the exhaustion from such a device of an amount of the LAP such that the remaining quantity thereof is insufficient to permit a medicinal reuse of the device. For devices in accordance with the present invention, medicinal reuse is avoided provided that the ratio of LAP in the device at the conclusion of the predetermined therapeutic duration to the amount of drug present in the device at the time of its insertion into the vagina or rectum is small. This ratio, hereinafter referred to as "P", while necessarily ranging in value from some number greater than zero to some number less than 1, will be less than about 0.42 for devices in accordance with the present invention.

By limiting P to a maximum value of about 0.42, an upper limit is placed on the ratio of the time following a first administration when the release rate of the device during a second attempted administration will be reduced to no more than one-half of the RF. When P is about 0.42, this ratio ($T_{50}/TD$) will necessarily be less than 0.5. Thus an attempted reuser would obtain a release rate of less than one-half of RR for any time greater than one-half of the predetermined therapeutic duration. When more severe constraints on non-reusability are required, devices in accordance with the present invention with lower values of P are provided capable of meeting such more stringent requirement. Thus, for example, where the ratio $T_{50}/TD$ must be less than one-quarter, values of P less than about one-quarter are selected.

In contrast to the situation where very stringent requirements on reusability are mandated, selection of P values somewhat higher than 0.42 are also provided in accordance with the present invention. For example, the value of P of about 0.6 may be preselected when the $T_{50}/TD$ ratio can range as high as about 1. Obviously, however, in those cases where the 50 percent effective dose ($ED_{50}$) of a LAP is as much as one-half the 100 percent effective dose ($ED_{100}$) of that LAP, the selection of P values as high as 0.6 will be so high as to permit as undesired medicinal reuse of certain of the devices prepared in accordance with the present invention.

In addition to providing a maximal value of $T_{50}/TD$, the preselected value for P likewise provides a minimum value for this ratio. Hence in order to guarantee that a proper constraint on $T_{50}/TD$ will be accomplished, a value of P so low that the desired $T_{50}/TD$ ratio falls above the minimum for that P value must be selected. For devices in accordance with the present invention the minimum and maximum bounds of the $T_{50}/TD$ ratio are expressed by the following inequalities:

$$T_{50}/TD < (ln2)P/(1-P) \qquad \text{Eq. 5}$$

$$T_{50}/TD > (ln2)P/(1-2P/3) \qquad \text{Eq. 6}$$

Within the range of values for $T_{50}/TD$ permitted by Eq. 5 and 6 above, devices constructed in accordance with the present invention further contain a $T_{50}/TD$ ratio determined by Eq. 6. For example when P is 0.25, $T_{50}/TD$ ratio will be between about 0.21 and 0.23.

The remaining design parameter for devices in accordance with the present invention, the thickness of the DBM, $T_{DBM}$, and the initial concentration of LAP are determined approxaimtely by Eq. 3 and 4, respectively.

Lastly, there is selected for use in accordance with the present invention a physiologically inert, resilient, and water-insoluble support means. The selection of a suitable material for the support means is as indicated above, made in part upon the physiological inertness of any prospective material. For example, materials known to irritate, react, or interact with rectal or vaginal epithelial tissues are avoided. Further, material used for the support means must exhibit a certain resiliency, such that the physical integrity of the medicated device upon insertion is maintained. Resilient materials preferably evidence some small degree of compressability or deformability such that facile administration is accomplished, but substantially rigid support means (e.g., high density polyethylenes and nylons) may optionally be employed. Finally, support means must be water insoluble, such that during the course of administration the secretions associated with vaginal or rectal epithelial tissue do not compromise the structural integrity of the device.

Just as the inner surface of the rate-controlling membrane is laminated onto the outer surface of the drug-bearing membrane, the inner surface of the drug-bearing membrane is laminated onto the support means. Accordingly, the shape, dimensions, and contours of the device of the present invention are essentially those of the support means. Hence, the support means must be adapted, contoured and dimensioned practicably for accomplishing the purposes of the instant invention. Specifically, the support means must facilitate the easy and comfortable insertion and withdrawal of the device into or from the vagina or rectum.

The support means of the present invention also exhibits numerous miscellaneous properties, namely being non-absorptive of the LAP and being constructed such that essentially the entire surface area would be in complete and intimate contact with vaginal or rectal epitherial tissues and associated secretions during administration. Accordingly, useful support means in accordance with the present invention are those which are non-concave or at least substantially so.

In view of the foregoing, clearly one especially convenient and well adapted support means for devices in accordance with the present invention are catamenial tampons. Commercially available catamenial tampons ordinarily contain an acceptably-sized surface area, are non-absorptive of lipophilic substances, and are water-insoluble. Moreover, catamenial tampons are specifically adapted, contoured and dimensioned for accomodation in the vagina.

Typically, catamenial tampons contain in addition to the corpus thereof a withdrawing means, ordinarily, simply a string. Devices in accordance with the present invention likewise preferably include as a further element thereof a withdrawing means, preferably a string or string-like appendage non-removably attached to the device itself.

There is accordingly provided medicated devices in accordance with the present invention which are surprisingly and unexpectedly capable of time-independent release of drug during a predetermined therapeutic duration, while avoiding the possibility of reuse of such devices thereafter. Moreover, extended uses of devices in accordance with the present invention beyond their intended therapeutic duration, results in a surprisingly and unexpectedly rapid reduction in release rate therefrom, whereby physiologically consequential dosages from such extended administrations are minimized, if not avoided. Thus, the coupling in devices in accordance with the present invention of a time-independent release rate with non-reusability provides a surprisingly and unexpectedly improved means for the induction of discrete events in mammalian reproductive cycle. Hence, such devices avoid the difficulties inherent in prior art time-independent release devices where reusability creates serious disposal problems and drug misuse problems.

BRIEF DESCRIPTION OF THE DRAWING

The drawing provides three views of a medicated device in accordance with the present invention, which drawing is not drawn to scale, but rather drawn to more clearly reflect the construction and operation of devices in accordance with the invention.

DETAILED DESCRIPTION OF THE DRAWING

Figure 1:
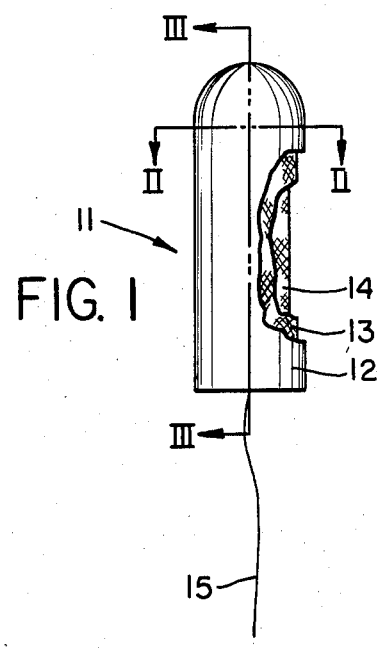
FIG. 1 depicts the device, further providing a cutaway view of the interior thereof, and depicts an embodiment exhibiting the optional withdrawing means.
Figure 3:
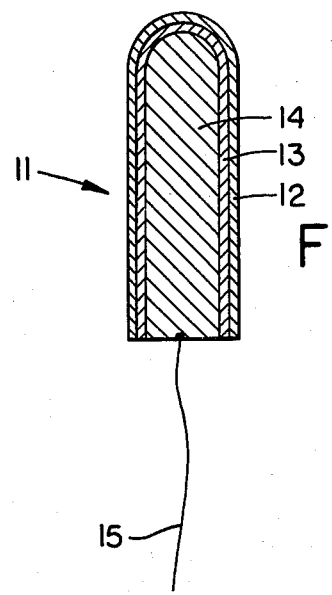
FIG. 3 provides a longitudinal cross-section of the device of FIG. 1.
Figure 2:
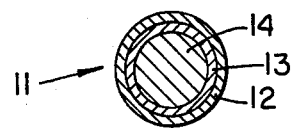
FIG. 2 provides a transverse cross-section of the device of FIG. 1.

The medicated device of the present invention has an outer surface (11) for its rate-controlling membrane or RCM (12). This rate-controlling membrane (RCM) is laminated onto the drug bearing membrane or DBM (13) and is substantially co-extensive therewith. The inner surface of this drug-bearing membrane (DBM) is then laminally affixed onto the support means (14), constituting a device in accordance with the present invention.

Finally the withdrawing means (15) is optionally attached to a device in accordance with the present invention, particularly being attached (as indicated in the drawing) non-removably to the support means.

DESCRIPTION OF THE PREFERRED EMBODIMENTS

EXAMPLE 1

Methodology for medicated device fabrication.

A. Polyurethanes are analyzed in a two cell diffusion chamber until two polyurethanes of substantially differing (i.e., 10–100 fold) diffusion coefficients are obtained. The polymer of higher diffusion coefficient is employed in the drug-bearing membrane or DBM while the polymer with the lower diffusion coefficient is reserved for the rate-controlling membrane or RCM.

B. A commercially available, compressed cotton catamenial tampon is selected as a support means. Membranes are prepared for lamination onto the tampon by a dip-coating method, employing an inverted test tube for membrane casting. Accordingly, a test tube is selected whose diameter is equal to or slightly less than the diameter that the catamenial tampon e.g., 5 ml. Firstly, the drug-bearing membrane is casted onto the test tube by dipping into a polymer-LAP containing solution. A water-miscible organic solvent, e.g., tetrahydrofuran is selected and polymer (3–20% by weight) and LAP (0.5–10% by weight) are added thereto. Thereafter, a test tube (e.g., 5 ml.) is inserted and slowly withdrawn from the solution. The withdrawal rate is adjusted to obtain the desired thickness ($T_{DBM}$). After drying and trimming, a second dip-coating is undertaken, employing a solution of the RCM polymer.

C. The laminated polymeric membranes prepared in part B are removed from the test tube by soaking in water (1–2 min.) and thereafter affixed to the catamenial tampon selected in part B. Securing of the laminated membranes onto the tampon may be accomplished by string tying at the base of the catamenial tampon (i.e., the juncture of the string withdrawing means to the tampon corpus).

In constructing devices in accordance with Example 1, the $C_{DBM}$, $T_{RCM}$, and $T_{DBM}$ are determined approximately from equations described above. These equations employ experimentally determined values for solubilities and diffusion coefficients and preselected values for P, RF, and therapeutic duration. In order to obtain the desired $C_{DBM}$, adjustments are made in the concentration of LAP in the solution employed in dip-coating the DBM. Likewise, LAP in the solution employed in dip-coating the DBM. Likewise, as indicated above, withdrawal rates of the test tube for coating both the DBM and RCM are adjusted so as to obtain the desired $T_{RCM}$ and $T_{DBM}$.

Adjustments in procedures to obtain desired values for $C_{DBM}$, $T_{TCM}$, $T_{DBM}$ are obtained by experimental casting, such procedures are well within the ordinary skill of the art.

Moreover, the approximate values for $C_{DBM}$, $T_{RCM}$, $T_{DBM}$ as given in the equation are employed in the construction of devices of the present invention. When such constructed devices exhibit the desired characteristics (e.g., for RF and TD), then values for $C_{DBM}$, $T_{RCM}$ and $T_{DBM}$ are precisely those indicated by the aforementioned equations. However, where performance characteristics are obtained from such constructed devices, values for $C_{DBM}$, $T_{RCM}$, and $T_{DBM}$ are adjusted by amounts not in excess of 10 percent until devices of desired performance are obtained. Such modifications in $C_{DBM}$, $T_{RCM}$, $T_{DBM}$ are accomplished in accordance with methods obvious to those of ordinary skill in the art. For example, devices in accordance with the present invention wherein the RF is inadequate will require reduction of the $T_{RCM}$ so that the desired, higher RF is exhibited. In such a case the approximate value for the $T_{RCM}$ given by the above equation therefore is adjusted upward by not more than about 10 percent, thus yielding the device with the desired RF.

We claim:

1. A medicated device adapted for single, acute, and rate-controlled vaginal or rectal administration to a female mammal of a therapeutic amount of LAP (lipophilic anti-luteal/oxytocic prostaglandin) effective to accomplish a discrete event in the mammalian reproductive cycle selected from the group consisting of
   (a) estrous induction,
   (b) menses induction,
   (c) cervical dilatation,
   (d) abortion,
   (e) labor induction, and
   (f) uterine evacuation subsequent to fetal death in utero or hydatidiform mole;
said administration being of a predetermined TD (therapeutic duration) of less than about 72 hours;
said administration resulting in the release of LAP from said device during the course of said administration at a predetermined, essentially time-independent RR (release rate) between about 1 μg and 1 mg per hour; and
said administration resulting in the exhaustion of said LAP from said device during the course of said treatment to the extent that the medicinal reuse of said device is essentially impossible; which comprises:
   (1) a flexible polymeric DBM (drug-bearing membrane), containing dissolved and suspended therethrough said LAP and being further characterized by:
- (a) a $D_{DBM}$ (diffusion coefficient of said DBM with respect to said LAP) and an $S_{DBM}$ (solubility in said DBM of said LAP);
- (b) an SA (surface area) of said DBM on the order of 10–50 cm², being sufficiently great such that the RF (release flux of said LAP released from said device), which RF is the quotient which is said RR divided by said SA, is substantially less than the absorption rate per unit area of said LAP by the rectal or vaginal epithelial tissues of said mammal in contact with said device during said administration; and
- (c) an essentially uniform $T_{DBM}$ (thickness of said DBM) and a $D_{DBM}$ (initial concentration of said LAP in said device), which $C_{DBM}$ is the quotient which is the amount of said LAP divided by the volume of said DBM;

(2) a flexible, polymeric RCM (rate controlling membrane), being laminated onto a first surface of said DBM and being substantially coextensive therewith, being further characterized by:
- (a) an $S_{RCM}$ (solubility in said RCM of said LAP) and an essentially uniform $T_{RCM}$ (thickness of said RCM); and
- (b) $D_{RCM}$ (diffusion coefficient of sad RCM with respect to said LAP), such that the $R_{RCM}$ (resistance of said RCM), which $R_{RCM}$ is the quotient which is said $T_{RCM}$ divided by the products of (i) K (partition coefficient between said DBM and RCM), which is the quotient which is said $S_{DBM}$ divided by said $S_{RCM}$ and (ii) said $D_{RCM}$, is at least very much greater than the $R_{DBM}$ (resistance of said DBM), which $R_{DBM}$ is the quotient which is said $T_{DBM}$ divided by said $D_{DBM}$; and (3) a physiologically inert, resilient, and water-insoluble support means, having the second surface of said DBM laminally affixed to at least a portion of the surface thereof; being adapted, contoured, and dimensioned for accomodation of the entirety of said DBM on the surface thereof and for easy and comfortable rectal or vaginal insertion and withdrawal of said device; being essentially non-absorptive of said LAP; and being of substantially non-concave construction, whereby the surface of said device upon insertion is in essentially complete and intimate contact with rectal or vaginal epithelial tissues and associated secretions;

said device being further characterized by
- (a) said $T_{RCM}$ being approximately $$D_{RCM} S_{RCM} / RF \qquad \text{Eq. 1}$$

wherein RF, $D_{RCM}$ and $S_{RCM}$ are as defined above;

- (b) said $T_{50}$, which is the time after TD for the RF to be reduced by 50 percent, being approximately $$(\ln 2)[P/1-P](TD) \qquad \text{Eq. 2}$$

wherein P is the ratio of the amount of LAP remaining in said device at TD to the initial amount of LAP in said device, said P being characterized by a preselected value less than about 0.42; and
wherein TD is as defined above;

- (c) said $[C_{DBM}]T_{DBM}$ being approximately $$[P/(1-P)][(RF)(TD)/S_{DBM}] - T_{RCM}2K \qquad \text{Eq. 3}$$

wherein K, TD, $T_{RCM}$, RF, and P are defined as above; and

- (d) said $C_{DBM}$ being approximately $$((RF)(TD)/(1-P)T_{DBM}) \qquad \text{Eq. 4}$$

wherein P, RF, TD, and $T_{DBM}$ are as defined above.

2. A medicated device in accordance with claim 1, wherein said LAP is 15-methyl-PGF₂, methyl ester.

* * * * *